(12) United States Patent
Kolb et al.

(10) Patent No.: US 10,365,208 B2
(45) Date of Patent: Jul. 30, 2019

(54) GAS SENSOR

(71) Applicants: Infineon Technologies AG, Neubiberg (DE); Fraunhofer-Gesellschaft Zur Foerderung Der Angewandten Forschung E.V., Munich (DE)

(72) Inventors: Stefan Kolb, Unterschleissheim (DE); Alfons Dehe, Reutlingen (DE); Jochen Huber, Wolfach (DE); Franz Jost, Stuttgart (DE); Horst Theuss, Wenzenbach (DE); Wilhelm Wiedmeier, Augsburg (DE); Juergen Woellenstein, Freiburg (DE)

(73) Assignees: Infineon Technologies AG, Neubiberg (DE); Fraunhofer-Gesellschaft Zur Foerderung Der Angewandten Forschung E.V., Munich (DE)

(*) Notice: Subject to any disclaimer, the term of this patent is extended or adjusted under 35 U.S.C. 154(b) by 258 days.

(21) Appl. No.: 15/079,840

(22) Filed: Mar. 24, 2016

(65) Prior Publication Data

US 2016/0282259 A1 Sep. 29, 2016

(30) Foreign Application Priority Data

Mar. 27, 2015 (DE) .................. 20 2015 002 315 U

(51) Int. Cl.
| | | |
|---|---|---|
| *G01N 21/17* | (2006.01) | |
| *G01N 29/02* | (2006.01) | |
| *G01N 29/24* | (2006.01) | |
| *G01N 29/30* | (2006.01) | |

(52) U.S. Cl.
CPC ....... *G01N 21/1702* (2013.01); *G01N 29/022* (2013.01); *G01N 29/2418* (2013.01); *G01N 29/30* (2013.01); *G01N 2021/1704* (2013.01); *G01N 2291/0256* (2013.01)

(58) Field of Classification Search
CPC ............. G01N 21/1702; G01N 29/022; G01N 29/2418; G01N 29/30; G01N 2021/1704; G01N 2291/0256
USPC ........... 73/24.02, 24.01, 24.06, 24.04, 31.05, 73/31.01
See application file for complete search history.

(56) References Cited

U.S. PATENT DOCUMENTS

| | | | |
|---|---|---|---|
| 2005/0262943 A1* | 12/2005 | Claydon .............. | G01N 29/022 73/579 |
| 2008/0277586 A1 | 11/2008 | Cardinale | |
| 2010/0020326 A1 | 1/2010 | Van Kesteren | |
| 2010/0147070 A1* | 6/2010 | Jun ....................... | G01N 27/121 73/335.05 |
| 2014/0260546 A1* | 9/2014 | Chen .................... | G01N 27/128 73/31.06 |
| 2014/0353780 A1* | 12/2014 | Perletti ................. | B81B 3/0021 257/416 |

(Continued)

FOREIGN PATENT DOCUMENTS

CN 101470074 A 7/2009

*Primary Examiner* — Natalie Huls
*Assistant Examiner* — Suman K Nath
(74) *Attorney, Agent, or Firm* — Eschweiler & Potashnik, LLC

(57) ABSTRACT

Shown is a gas sensor including a sensor element, a measurement chamber and an emitter element. The sensor element has a MEMS membrane which is arranged in a first substrate region. Furthermore, the measurement chamber is embodied to receive a measurement gas.

11 Claims, 16 Drawing Sheets

(56) References Cited

U.S. PATENT DOCUMENTS

| | | | |
|---|---|---|---|
| 2015/0101395 A1* | 4/2015 | Dehe | G01N 29/2418 |
| | | | 73/24.02 |
| 2015/0123000 A1 | 5/2015 | Sagberg | |
| 2015/0213699 A1* | 7/2015 | Bell | G01J 5/10 |
| | | | 250/338.1 |
| 2015/0285772 A1* | 10/2015 | Park | G01N 33/0031 |
| | | | 73/31.05 |

\* cited by examiner

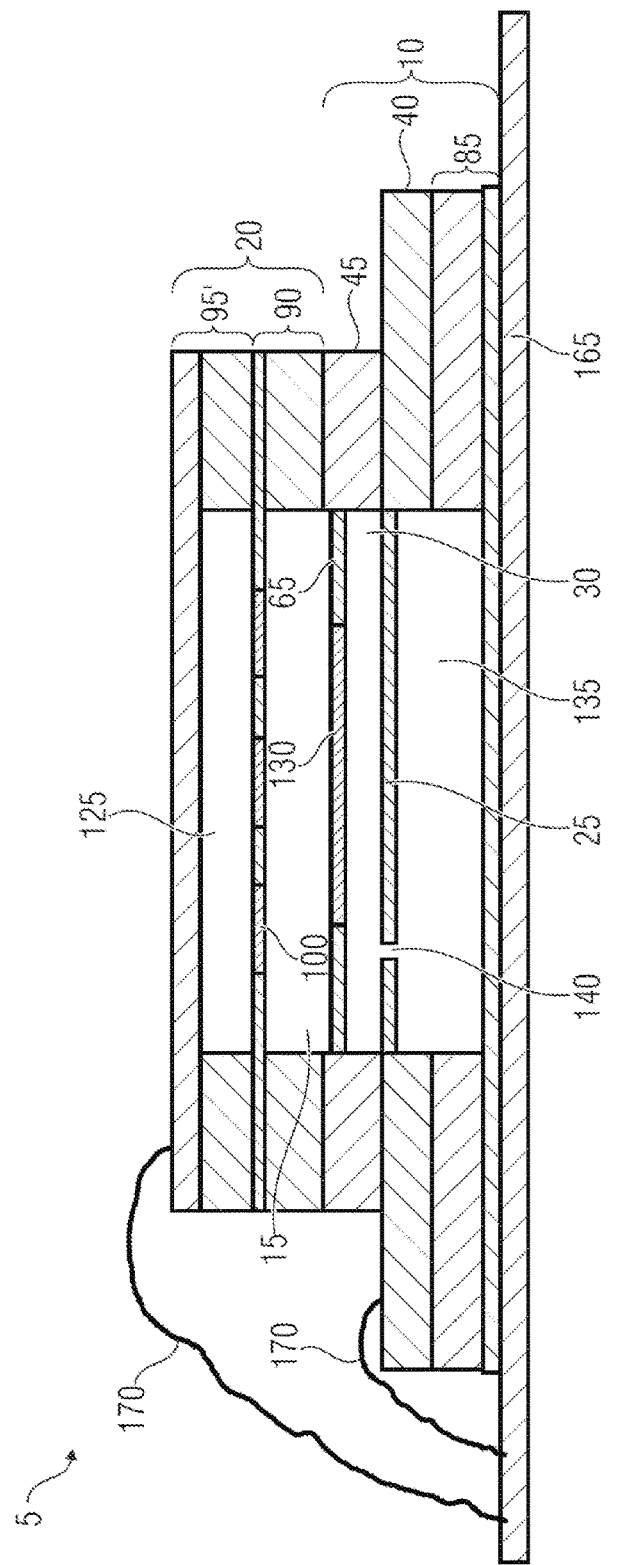

GAS SENSOR

CROSS REFERENCE TO RELATED APPLICATIONS

This application claims priority to German Application No. 20 2015 002 315.0, filed on Mar. 27, 2015, and incorporated herein by reference in its entirety.

FIELD

The present disclosure describes a gas sensor which has a MEMS membrane. Exemplary embodiments disclose a PAS (photoacoustic sensor) module, which uses a MEMS (microelectromechanical system) multi-wafer concept.

BACKGROUND

A MEMS device, which is also referred to as a microelectromechanical system, is often used as a sensor, for example as acceleration sensors, pressure sensors or sound wave sensors (microphone). All of these MEMS devices have a movable element, for example a membrane or a cantilever, wherein the movement of the movable element, as is caused, for example, by a pressure change or acceleration, can be detected capacitively. Thus, a conventional variant of a MEMS device comprises a movable electrode as a movable element and a stationary electrode lying opposite to the movable electrode such that a change in the distance between the two electrodes (due to the movement of the movable element) can lead to a capacitive change.

Previous gas sensor systems use components with dimensions in the millimeter to centimeter range. The components, e.g. an infrared emitter, therefore have comparatively large thermal masses, as a result of which high powers are required to operate the gas sensors. These make the systems sluggish and only allow very small duty cycles. Therefore, options for a quick calibration and a quick measurement are restricted.

Therefore, there is a need to develop an improved concept for gas sensors.

SUMMARY

Exemplary embodiments disclose a gas sensor which comprises a sensor element, a measurement chamber and an emitter element. The sensor element has a MEMS membrane, wherein the MEMS membrane is arranged in a first substrate region. Furthermore, the measurement chamber is embodied to receive a measurement gas. The emitter element is embodied to emit electromagnetic radiation, wherein the electromagnetic radiation passes over a radiation path, which includes the measurement chamber proceeding from the emitter element. Moreover, the emitter element and the sensor element are arranged in a stationary manner with respect to one another, i.e. they are mechanically connected to one another for example.

Advantageously, a combination of components manufactured using MEMS technology is used for an e.g. miniaturized gas sensor. These components can be connected in a so-called wafer stack or substrate stack and can form an emitter and a sensor which, in turn, can be connected to one another. By way of example, the gas sensor can be a PAS sensor (photoacoustic sensor), which uses the photoacoustic effect.

The photoacoustic effect is a physical effect which optoacoustics makes use of. It describes the conversion of light energy into acoustic energy (sound). If a propagation medium, e.g. a gas, is irradiated with light, some of the light energy is received (absorbed) by the medium and converted into heat. As a result of thermal conduction, the energy is distributed in the medium after a finite period of time and a minimally increased temperature sets in in the medium. There is, inter alia, an increase in volume as a result of the heat supply. There is periodic heating and cooling if the medium is irradiated by a sequence of light flashes or, in general, by pulses of electromagnetic radiation. This constant change in volume expansion and reduction constitutes a source of sound. This can be body-borne sound in a solid body or normal sound in gas.

Advantages emerge as a result of the very small dimensions of the overall sensor system, as a result of which very small thermal masses of the sensor system can be realized. As a result, the power intake is reduced and high switching speeds are rendered possible, from which a very large duty cycle and hence a long overall service life result. Likewise, a shorter measurement cycle of a measurement emerges from the higher switching speeds, as a result of which more measurements can be carried out in the same period of time. The described gas sensor therefore meets the highest quality requirements and has an increased service life compared to conventional gas sensors.

Exemplary embodiments disclose a gas sensor which comprises a sensor element, a measurement chamber and an emitter element. The sensor element has a MEMS membrane and a reference chamber with a reference fluid situated therein, wherein the MEMS membrane is arranged in a first substrate region and a cavity of the reference chamber is arranged in a second substrate region. The first and second substrate regions are hermetically sealed from, and connected to, one another. The measurement chamber is embodied to receive a measurement gas. The emitter element is embodied to emit electromagnetic radiation, wherein the electromagnetic radiation passes over a radiation path, which includes the measurement chamber and the reference chamber proceeding from the emitter element, wherein the measurement chamber is spatially separated from the reference chamber by a layer through which electromagnetic radiation can pass. Moreover, the emitter element and the sensor element are mechanically connected to one another. The embodiment with a reference chamber and reference gas present therein is advantageous since the pressure measurement takes place in the sealed and known reference volume and hence a greater number of realization options are available. The background is a variable adjustment option for the MEMS membrane or the sensor element to a complete or partial selectivity of the measurement gas or an avoidance of cross sensitivities. Thus, the sensor element only reacts to the absorption wavelength of the reference gas, provided that the reference gas is pure and no "interference gases" are present. If an interference gas is present, a cross sensitivity may occur where the absorption wavelengths of the reference gas (or of the measurement gas) and of the interference gas overlap. By way of example, when measuring $CO_2$, there is a cross sensitivity to moisture at a wavelength of approximately 2.2 μm since the absorption bands of carbon dioxide and water overlap there.

Exemplary embodiments show that the MEMS membrane is embodied to convert energy of the electromagnetic radiation, present in the reference chamber, into an output signal. By way of example, the conversion is carried out by virtue of the MEMS membrane being embodied to have a deflection which is dependent on the energy of the electromagnetic radiation present. This is advantageous since the electromagnetic radiation excites the reference fluid to a larger vibration and hence the increased particle movement or an increased pressure in the reference chamber can be measured by the MEMS membrane or a sensor formed with the MEMS membrane.

In accordance with exemplary embodiments, the emitter element is embodied to emit the electromagnetic radiation in a pulsating manner with a frequency that is typically greater than 0.1 Hz or greater than 0.5 Hz or greater than 1 Hz. This is advantageous since this therefore allows an increased number of measurements to be carried out within the same period of time. Furthermore, the measurement density e.g. in the case of continuous measurements is thus increased, with a change in a measurement gas in the measurement chamber therefore being detected more quickly.

Exemplary embodiments furthermore disclose the emitter element, which comprises a first and a second substrate region, wherein the first substrate region has an emitter unit, which is embodied to emit the electromagnetic radiation. The second substrate region has a cavity, which is embodied to minimize a thermal mass of the emitter element. This is advantageous as the already described quick switching times of the emitter element can therefore be achieved. Furthermore, an unnecessary heating of the sensor is reduced. A heating of the sensor can lead to quicker degradation. A cooling of the gas sensor for dissipating excessive heat can therefore have smaller dimensions or be completely removed.

Moreover, the sensor or the MEMS membrane can preferably lie outside a direct beam path of the electromagnetic radiation emitted by the emitter in order to reduce heating of the MEMS membrane by the direct electromagnetic radiation. A further exemplary embodiment discloses the gas sensor with a shadow mask, which is arranged in the radiation path, wherein the shadow mask is embodied to reduce direct electromagnetic radiation onto the MEMS membrane from the emitter element. This is advantageous as this therefore delays a degradation of the MEMS membrane since a substantially smaller part of the latter is exposed to the electromagnetic radiation. Furthermore, a pressure equalization chamber situated behind the MEMS membrane is heated less strongly by the electromagnetic radiation, as a result of which a sensitivity or accuracy of the gas sensor is ensured over a longer period of time.

In accordance with further exemplary embodiments, the emitter element and the sensor element are arranged in a projection plane extending laterally with respect to the emitter element and the sensor element. Here, the emitter element and the sensor element are arranged in a housing which is embodied to reflect the electromagnetic radiation from the emitter element onto the sensor element. This arrangement is advantageous since it is therefore possible to realize extremely flat gas sensors. Here, the measurement chamber of the gas sensor can be embodied as a cavity in the housing. Furthermore, it is advantageous to embody the first substrate region of the sensor element and a first substrate region of the emitter element on the same substrate and/or to embody the second substrate region of the sensor element and a second substrate region of the emitter element on the same substrate. This is advantageous since this allows manufacturing steps relating to the same substrate plane in the sensor element and in the emitter element to be carried out together in one manufacturing step. Hence, a production of these gas sensors is simplified, as a result of which an increase in the productivity is achieved.

In accordance with a further exemplary embodiment, the emitter element and the sensor element are arranged in a projection plane extending in the thickness direction with respect to the emitter element and the sensor element, wherein the second substrate region of the sensor element is connected to the emitter element in a hermetically sealed manner. This is advantageous as a minimum overall size of the gas sensor is therefore obtained. Here, a cavity in the emitter element and/or a cavity between the emitter element and the sensor element can form the measurement chamber. If the measurement chamber is integrated into the emitter element, the gas sensor has a minimum height in the thickness direction. If the cavity is embodied between the emitter element and the sensor element, the emitter element can be spatially separated from the measurement gas, as result of which a possibly increased degradation of the sensor element by the measurement gas is avoided.

Exemplary embodiments furthermore disclose the gas sensor, in which contacts of the emitter element and of the sensor element are guided by means of a through semiconductor via (TSV) within the emitter element and the sensor element to a common substrate plane and embodied at a main surface region of the gas sensor that is accessible from outside. This is advantageous since contacts of the gas sensor are therefore only embodied at one position of the gas sensor and therefore simplify contacting.

Exemplary embodiments furthermore describe that contacts of the emitter element and the sensor element are embodied laterally at a surface region of the emitter element and the sensor unit, wherein a printed circuit board is arranged parallel to a thickness direction of the emitter element and the sensor element and contacts the laterally embodied contacts. This is advantageous since, for example, the gas sensor can be arranged on the printed circuit board without further contacting materials and can be connected electrically to the latter.

In accordance with further exemplary embodiments, the emitter element has an emitter unit for emitting the electromagnetic radiation, which emitter unit is an infrared emitter.

Further exemplary embodiments disclose the gas sensor, wherein the MEMS membrane forms a micromechanical capacitive sensor. By way of example, the micromechanical capacitive sensor is a microphone.

DETAILED DESCRIPTION OF THE DRAWINGS

Embodiments of the present disclosure are explained below, with reference being made to the attached drawings. In detail:

FIG. 1c shows a schematic side view of a gas sensor in an arrangement of the emitter element and the sensor element deviating from the one in FIG. 1a;

FIG. 5c shows a schematic illustration of a gas sensor in accordance with a deviating exemplary embodiment with a reference chamber and with exemplary contacting of the gas sensor;

DETAILED DESCRIPTION

In the following description of the figures, identical elements or elements with identical effect are provided with the same reference signs, and so the description thereof is interchangeable in the different exemplary embodiments.

Figure 1A:
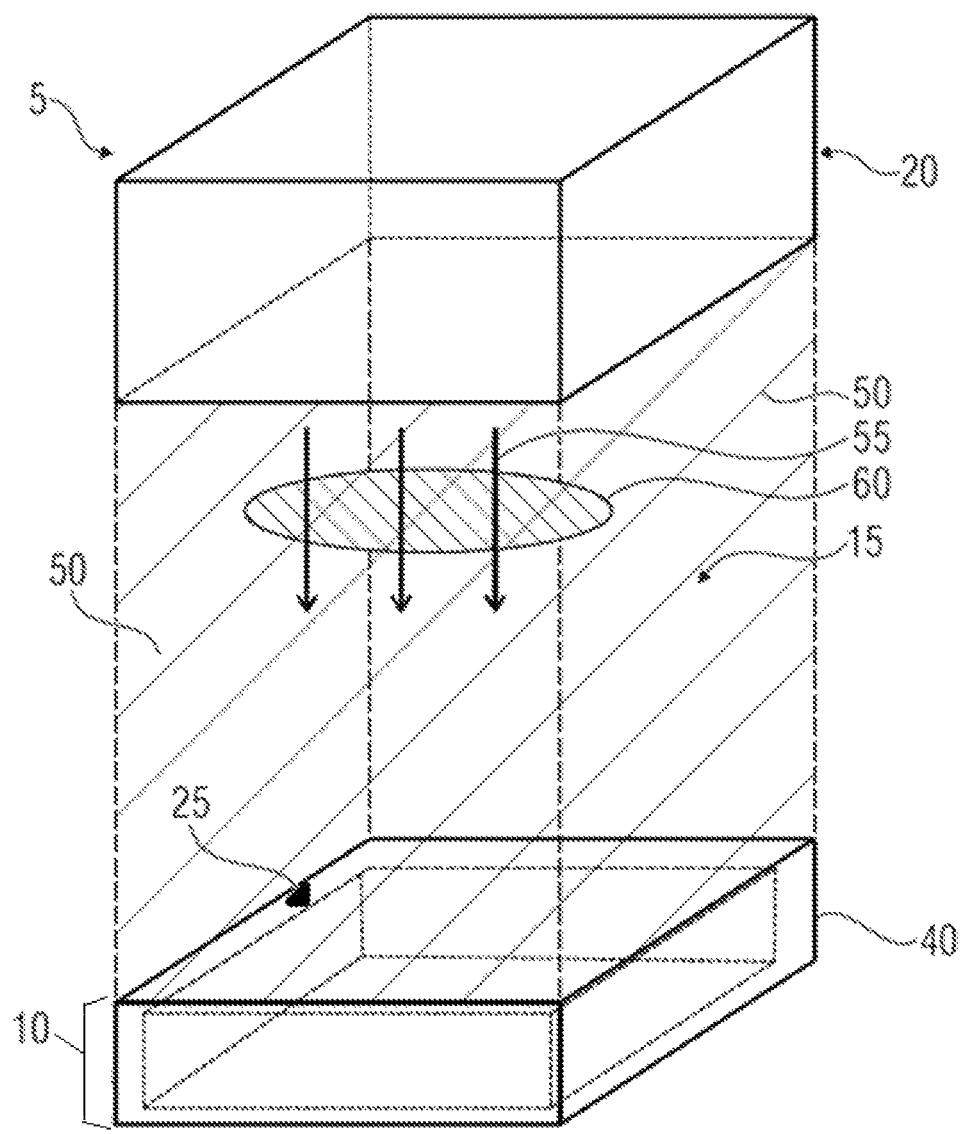
FIG. 1a shows a schematic side view of a gas sensor.

FIG. 1a shows a gas sensor 5 with a sensor element 10, a measurement chamber 15 and an emitter element 20. The sensor element 10 has a MEMS membrane 25, which is arranged in a first substrate region 40. The measurement chamber 15 is embodied to receive a measurement gas 50. Moreover, the sensor element 10 and the emitter element 20 can have a hermetically sealed connection in accordance with one exemplary embodiment such that a hermetically sealed measurement chamber 15 is formed. This can increase the service life of the emitter element 20 or of the whole gas sensor since the latter is operated in a protective atmosphere. The same effect can also be achieved by a housing which surrounds the gas sensor. By way of example, the MEMS membrane can form a micromechanical capacitive sensor such as e.g. a microphone. The micromechanical capacitive sensor is embodied to measure a deflection of the MEMS membrane in relation to a counter electrode (not shown here) capacitively.

Furthermore, FIG. 1a shows the emitter element 20, e.g. an infrared emitter, which may be realized as a MEMS element, which is embodied to emit electromagnetic radiation 55. The electromagnetic radiation 55 passes over a radiation path 60, which includes the measurement chamber 15 proceeding from the emitter element 20. Furthermore, the emitter element 20 and the sensor element 10 are mechanically interconnected. The hermetically sealed connection is optional since the confinement of the measurement gas in a volume can also be achieved, for example, by way of a housing shown in FIG. 3. Furthermore, there are also exemplary embodiments in which the confinement of the measurement gas is optional. If the measurement gas is not present in a sealed volume, it is advantageous to embody the measurement gas or the measurement volume as an acoustic high-pass filter so that the photoacoustic signals of the measurement gas act on the MEMS membrane and scattering into the free space is avoided. Therefore, the acoustic high-pass filter renders performing continuous measurements in the case of a measurement gas in free space possible. In other words, a pressure change in an unsealed volume or reference volume of the detector can be measured if the sensor element is embodied as a high-pass filter. Therefore, continuous measurements are possible, for example with a sealed detector or with an embodiment of the detector as a high-pass filter. The described exemplary embodiment constitutes a gas sensor which can be constructed to be very small since it is realized in the absence of the exemplary embodiments with a reference chamber described below.

An improved measurement result can be achieved by separating the heat transfer from the emitter element 20 via the measurement gas 50. In other words, it may be advantageous if heating of the measurement gas 50 or an effect of a pressure change on the MEMS membrane due to the heating of the measurement gas is avoided. This can be achieved by closing off the emitter element or the sensor element. If the emitter element or the emitter is embodied in a closed-off manner, by a vacuum or an inert protective gas between an emitter unit, for example a heating wire, can be arranged, which allows infrared radiation from the emitter element to the measurement gas, but prevents or at least reduces heat propagation. If the sensor element has a closed-off embodiment and the emitter element 20 is open, the measurement gas is heated but a pressure change does not act on the MEMS membrane. In both cases, a photoacoustic signal can be measured free from a superposition of an expansion of the measurement gas caused by the heating. It is likewise possible to hermetically seal the emitter element and the sensor element in each case.

The described combinations of emitter element and sensor element can be subsumed under the term multi-wafer concept. It enables any combination of sealed and open elements, which in each case form an open or closed emitter or sensor element. Likewise, the measurement chamber can optionally also be embodied in a closed volume. The combinations of the elements may be arbitrary. Moreover, the emitter element and/or the sensor element can be embodied, per se, from layers of different substrate elements or wafers. An exemplary realization is described in relation to FIGS. 2a-e.

Figure 1B:
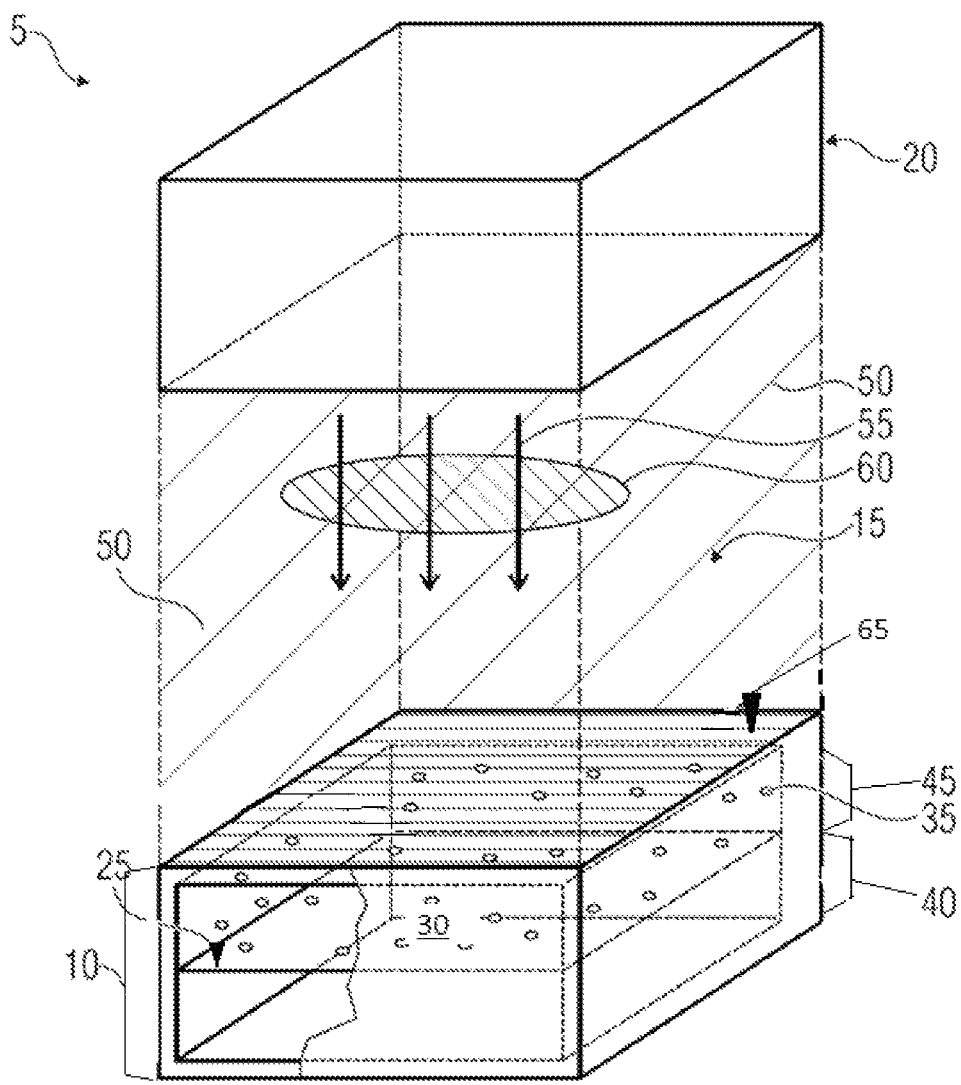
FIG. 1b shows a schematic side view of a gas sensor with a reference chamber.

FIG. 1b shows a gas sensor 5 with a sensor element 10, a measurement chamber 15 and an emitter element 20. The sensor element 10 has a MEMS membrane 25 and a reference chamber 30 with a reference fluid 35 situated therein. The MEMS membrane 25 is arranged in a first substrate region 40 and a cavity of the reference chamber 30 is arranged in a second substrate region 45. The measurement chamber 15 is embodied to receive a measurement gas 50. Furthermore, the first and second substrate regions 40, 45, which form the sensor element 10, are hermetically sealed from, and connected to, one another. Moreover, the sensor element 10 and the emitter element 20 can also have a hermetically sealed connection in accordance with one exemplary embodiment such that a hermetically sealed measurement chamber 15 is formed. This can increase the service life of the emitter element 20.

Furthermore, FIG. 1b shows the emitter element 20 which is embodied to emit electromagnetic radiation 55. The electromagnetic radiation 55 passes over a radiation path 60, which includes the measurement chamber 15 and the reference chamber 30 proceeding from the emitter element 20. In order to spatially separate the measurement gas and the reference fluid from one another, a layer 65 through which electromagnetic radiation 55 can pass is arranged between the reference chamber 30 and the measurement chamber 15. Furthermore, the emitter element 20 and the sensor element 10 are mechanically connected to one another.

By way of example, the reference fluid is a gas mixture which comprises a gas to be detected, e.g. $CO_2$ (carbon dioxide), CO (carbon monoxide), $NO_x$ (nitrogen oxide) etc., and optionally a buffer gas. By way of example, the buffer gas serves as a further reference gas by virtue of it extending the selectivity of the reference cell to a gas mixture or a further gas. Thus, in addition to the gas to be detected, one or more further gases may be present in the reference chamber such that the gas sensor reacts sensitively to a measurement gas which comprises the gases present in the reference gas. Furthermore, it is possible to introduce moisture into the reference chamber in order to determine a moisture content of the measurement gas. Expressed differently, it serves as an element for modifying or optimizing the transmission path, wherein the transmission path has the following steps. Proceeding from a temperature or electromagnetic radiation of the emitter element 20, a pressure change is generated in the reference chamber 30, wherein the pressure change depends on the absorption of the electromagnetic radiation by the measurement gas (e.g. in an inversely proportional manner). The pressure change in the reference chamber can be measured by a deflection of the membrane in the sensor element 10. Furthermore, a sensitivity of the gas sensor 5 or of the sensor element 10 can be adjusted by way of the buffer gas such that the desired sensitivity is obtained in the case of an expected oversteer or understeer of the MEMS membrane, for example by a reduction or increase in the buffer gas component.

Exemplary embodiments show the MEMS membrane 25, which is embodied to convert energy of the electromagnetic radiation present in the reference chamber 30 into an output signal. The output signal can be generated on the basis of a deflection which is dependent on the energy of the electromagnetic radiation present. Accordingly, the MEMS membrane can form, for example, a micromechanical capacitive sensor such as e.g. a microphone. The micromechanical capacitive sensor is embodied to measure a deflection of the MEMS membrane, for example capacitively, in relation to a counter electrode (not shown here).

Figure 1C:
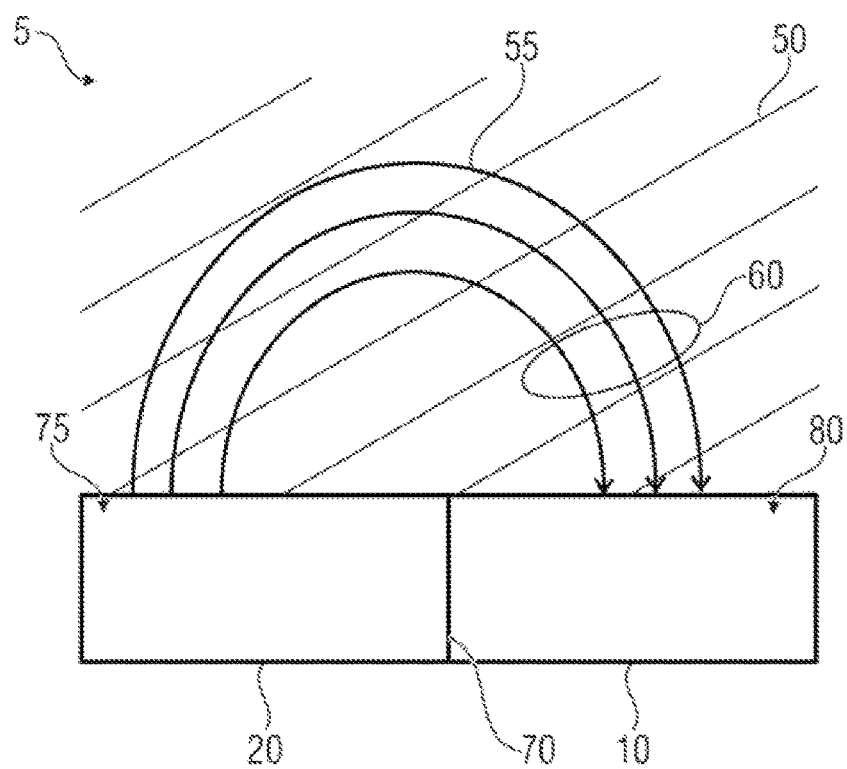
Figure 3:
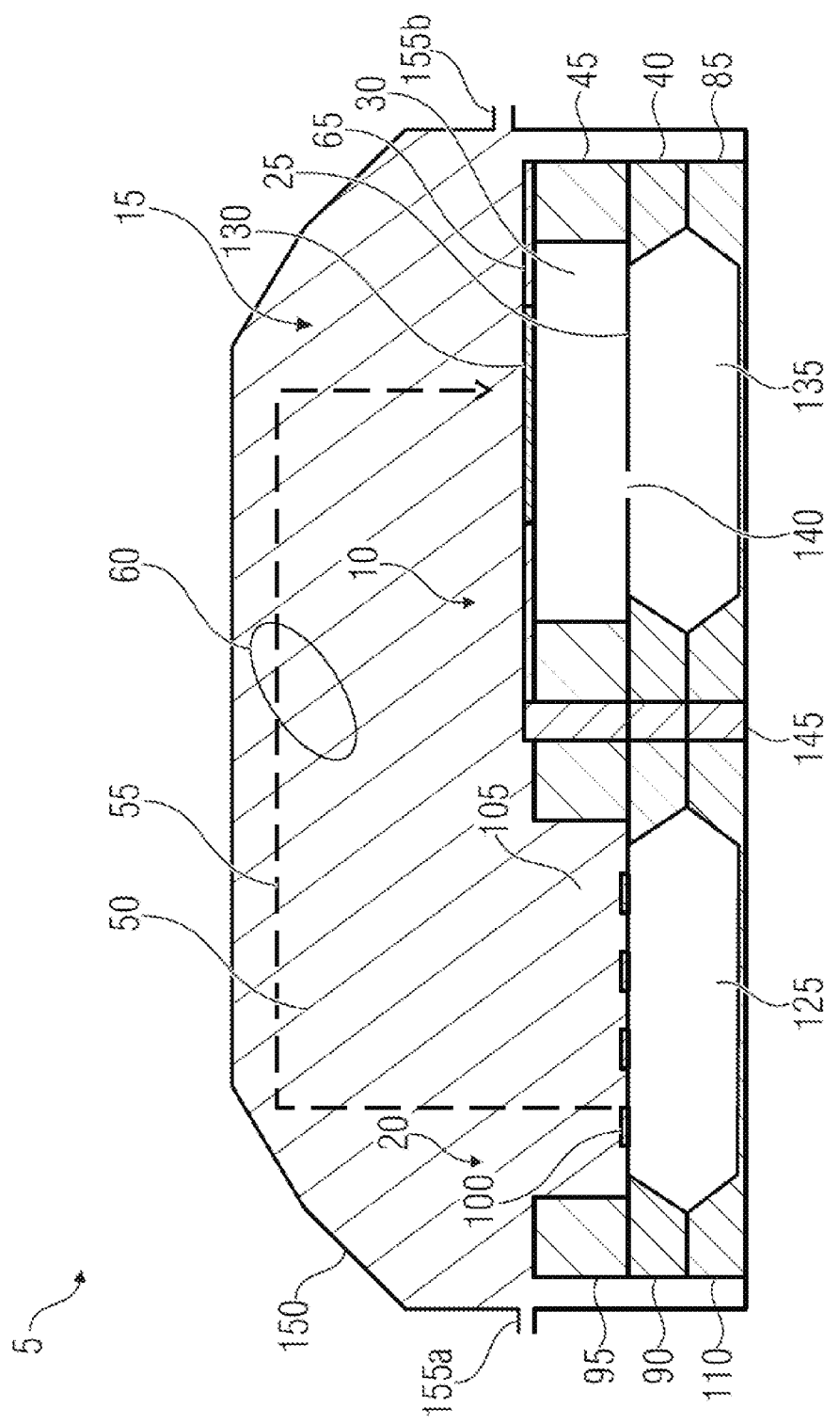
FIG. 3 shows a schematic illustration of a gas sensor in a housing, wherein the emitter element and the sensor element are arranged next to one another.

FIG. 1c shows a schematic illustration of the gas sensor 5 with an arrangement of the emitter element and the sensor element deviating from the one in FIG. 1a. FIG. 1c shows an arrangement of the emitter element 20 and the sensor element 10 along a projection line which extends laterally through the emitter element and the sensor element. Here, the emitter element 20 and the sensor element 10 are connected to one another at a laterally extending main surface region 70. In accordance with one exemplary embodiment, the radiation path 60 of the electromagnetic radiation 55 passes through the measurement gas 50 adjoining the emitter element 20 and the sensor element 10. The curvature or deflection of the electromagnetic radiation 55 from the main surface region 75 of the emitter element, at which the electromagnetic radiation is emitted, onto the main surface region 80 of the sensor element, at which the electromagnetic radiation enters into the sensor element, is brought about, for example, by way of reflecting elements (not shown here), such as e.g. the inner side of a housing which has a reflecting action for the electromagnetic radiation 55. FIG. 3 shows an exemplary embodiment of this arrangement.

Figure 2A:
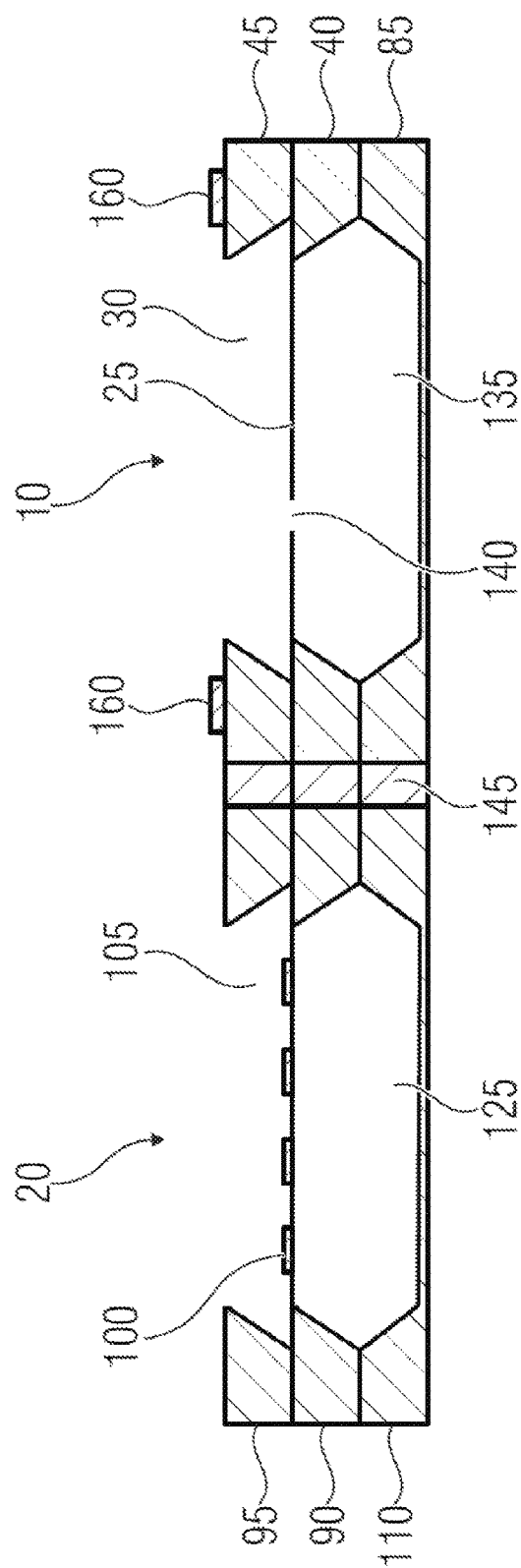
FIG. 2a shows, in a cross section, a schematic illustration of an emitter element and a sensor element which are used in a gas sensor.

FIG. 2a shows a schematic illustration of the emitter element 20 and of the sensor element 10, which are used in a gas sensor in accordance with exemplary embodiments. In addition to the first substrate region and the second substrate region 45, the sensor element 10 can additionally have a third substrate region 85 which, in the exemplary embodiment shown here, constitutes a boundary element of the sensor element 10. Analogously to the sensor element, the emitter element can also have a first substrate region 90 and a second substrate region 95, wherein the first substrate region 90 has an emitter unit 100 which is embodied to emit the electromagnetic radiation 55. By way of example, the emitter unit 100 is an infrared emitter (IR emitter), which can be realized by a meandering arrangement of a heating wire. The second substrate region 95 of the emitter element has a cavity 105, which is embodied to minimize a thermal mass of the emitter element. In accordance with further exemplary embodiments, the second substrate region 55 of the emitter element can have a material transmissive to the electromagnetic radiation 55 in addition or as an alternative to the cavity 105. Furthermore, the emitter element 20 also has a third substrate region 110, which forms a boundary element of the emitter element. Moreover, it should be noted that the exemplary embodiments described with respect to FIGS. 2b-d can also be applied to FIG. 2a.

In accordance with this arrangement, the emitter element 20 can form a black body. An ideal black body completely absorbs incident electromagnetic radiation of any wavelength and re-emits the received energy as electromagnetic radiation with a characteristic spectrum that only depends on the temperature.

Figure 2B:
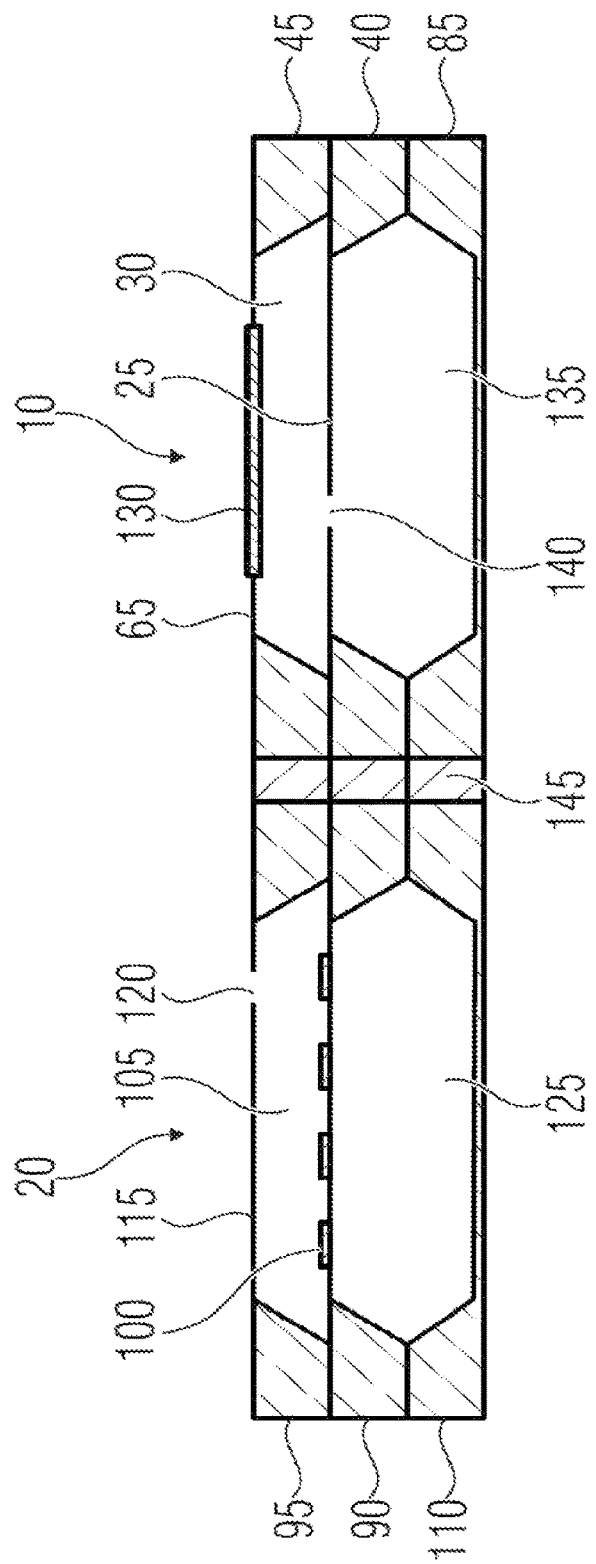
FIG. 2b shows a schematic illustration of an emitter element and a sensor element which are used in a gas sensor, in accordance with an exemplary embodiment with a reference chamber.

FIG. 2b shows a schematic illustration of the emitter element 20 and of the sensor element 10, which are used in a gas sensor in accordance with exemplary embodiments. In addition to the first substrate region and the second substrate region 45, the sensor element 10 can additionally have a third substrate region 85 which, in the exemplary embodiment shown here, constitutes a boundary element of the sensor element 10. Analogously to the sensor element, the emitter element can also have a first substrate region 90 and a second substrate region 95, wherein the first substrate region 90 has an emitter unit 100 which is embodied to emit the electromagnetic radiation 55. By way of example, the emitter unit 100 is an infrared emitter (IR emitter), which can be realized by a meandering arrangement of a heating wire. The second substrate region 95 of the emitter element has a cavity 105, which is embodied to minimize a thermal mass of the emitter element. In accordance with further exemplary embodiments, the second substrate region 95 of the emitter element can have a material transmissive to the electromagnetic radiation 55 in addition or as an alternative to the cavity 105. Furthermore, the emitter element 20 also has a third substrate region 110, which forms a boundary element of the emitter element.

In accordance with this arrangement, the emitter element 20 can form a black body. An ideal black body completely absorbs incident electromagnetic radiation of any wavelength and re-emits the received energy as electromagnetic radiation with a characteristic spectrum that only depends on the temperature.

Figure 4A:
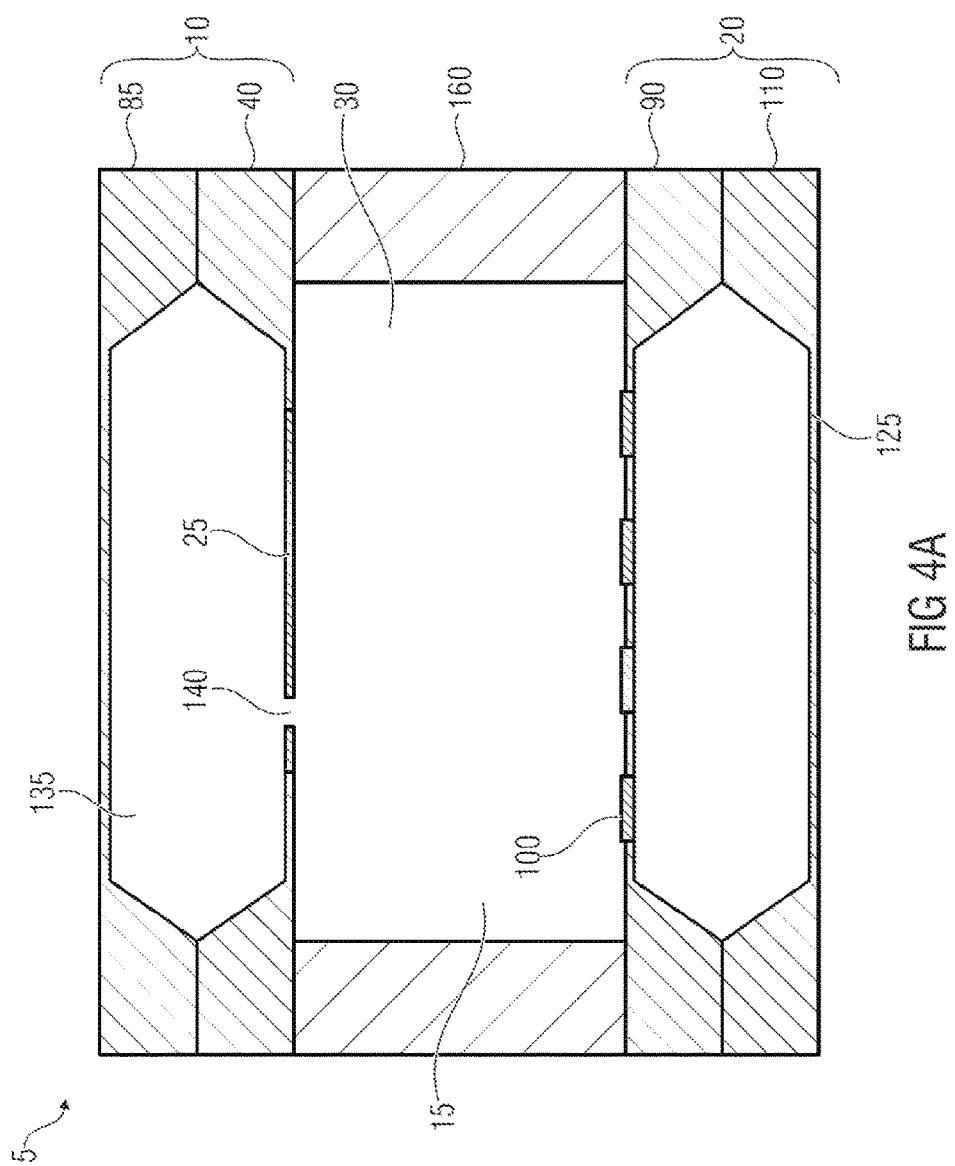
FIG. 4a shows a schematic illustration of a gas sensor in accordance with one exemplary embodiment, wherein the emitter element and the sensor element are stacked in the thickness direction.
Figure 4B:
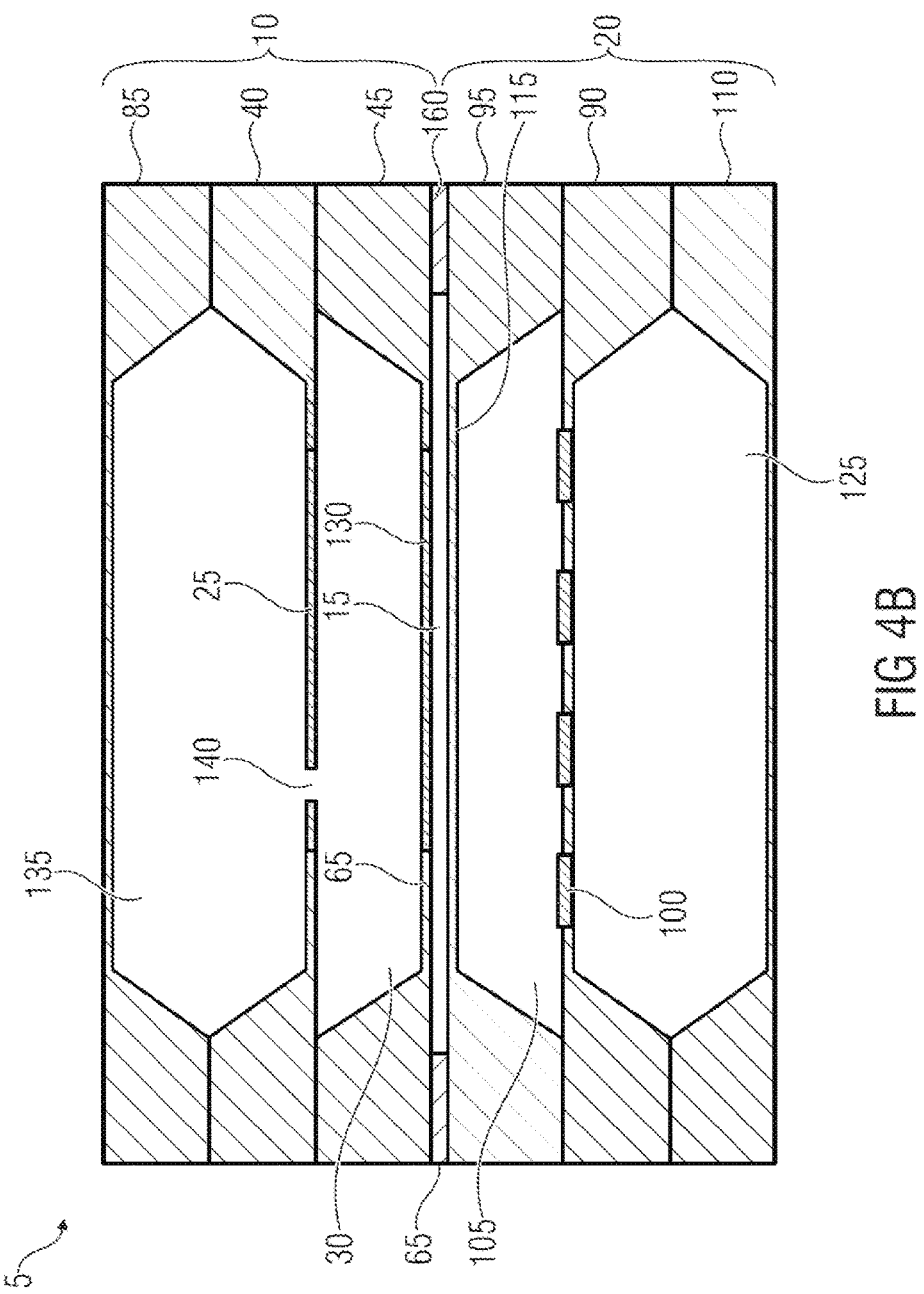
FIG. 4b shows a schematic illustration of a gas sensor in accordance with one exemplary embodiment with a reference chamber, wherein the emitter element and the sensor element are stacked in the thickness direction.

Analogous to the layer 65 of the second substrate region of the sensor element transmissive to the electromagnetic radiation, the second substrate region 95 of the emitter element can likewise have a layer 115 transmissive to the electromagnetic radiation in accordance with exemplary embodiments, wherein FIG. 4b shows an exemplary embodiment in which the layers 65 and 115 form the measurement chamber. Furthermore, the layer 115 can optionally have an opening 120. The opening 120 can provide access to the cavity 105 for the reference fluid such that an absorption path for the temperature radiation emitted by the emitter element is increased. Furthermore, cavities are optionally formed in the first and third substrate regions of the emitter element, which cavities are embodied in each case to reduce a thermal mass of the sensor element and to form a hollow space 125 for realizing the black body. Optionally, the hollow spaces 125 and 105 can be filled with a buffer gas, which is embodied to minimize a degradation of the emitter unit and/or to improve a quality of the emitter element. In this exemplary embodiment, it is advantageous to embody the layer 115 without an opening 120 in order to separate the buffer gas from the measurement gas.

Furthermore, arranging a shadow mask 130 in the radiation path 60 (not plotted here) is likewise optional, said shadow mask being embodied to reduce direct electromagnetic radiation from the emitter element to the MEMS membrane 25. However, the shadow mask permits the entry of the electromagnetic radiation into the reference chamber. To this end, the shadow mask, for example, only covers part of the layer of the sensor element transmissive to the electromagnetic radiation or, in accordance with the exemplary embodiment described in FIG. 2e, it is arranged in front of the MEMS membrane within the reference chamber. Expressed differently, an optional shadow mask does not shadow the reference chamber 30 but only the membrane 25. Advantageously, the layer 65 transmissive to the electromagnetic radiation, e.g. a glass pane, is coated or blackened to this end in a region of a projection line which extends to the membrane 25 in the thickness direction. Therefore, the electromagnetic radiation 55 can excite the reference fluid in the reference chamber 30 through the regions adjacent to the shadow mask 130, but the direct electromagnetic irradiation of the MEMS membrane 25 is significantly reduced. As a result, the MEMS membrane heats up to a significantly lesser extent, as a result of which wear-and-tear or an error signal of same, caused by a heating and a deflection of the membrane caused thereby (comparable to the effect in a bimetal), is reduced.

Furthermore, the shadow mask 130 reduces the heating of a pressure equalization chamber 135. The pressure equalization chamber 135 is connected to the reference chamber 30 by way of an opening 140 in the MEMS membrane 25. There is a slow gas exchange between the reference chamber and the pressure equalization chamber through the opening such that changing pressures in the reference chamber and the pressure equalization chamber are equalized over a relatively long period of time and pre-tensioning of the MEMS membrane 25, which changes over the long period of time, is avoided. Quick pressure changes cannot be equalized by way of the opening 140, and so the MEMS membrane 25 or the sensor element 10 is able to measure the quick changes. It should be noted that the shadow mask 130 is optional in all exemplary embodiments shown, even if same as plotted in the associated drawings.

Advantageously, the substrate regions of the sensor element and of the emitter element can contain silicon. Therefore, the same substrate regions of the sensor element and of the emitter element can be produced in a common MEMS production method within the scope of one production method. In accordance with exemplary embodiments, the substrate regions produced separately are stacked and arranged as a wafer stack or substrate stack. In order to fasten the substrate regions, same can be connected to one another, for example by means of anodic bonding or glass frit bonding, such that connection elements depending on the method are formed between the substrate regions (e.g. wafers). The second substrate regions of the sensor element 45 or of the emitter element 95 (top layers) or the first substrate regions of the sensor element 85 or of the emitter element 110 (bottom layers) can also be embodied as a glass wafer or have a glass component, for example in the form of a window.

In the shown arrangement, the sensor element 10 and the emitter element 20 can be operated laterally next to one another, for example within a housing, as a pressure sensor (cf. FIG. 3) or, alternatively, be singulated by way of saw marks 145.

Figure 2C:
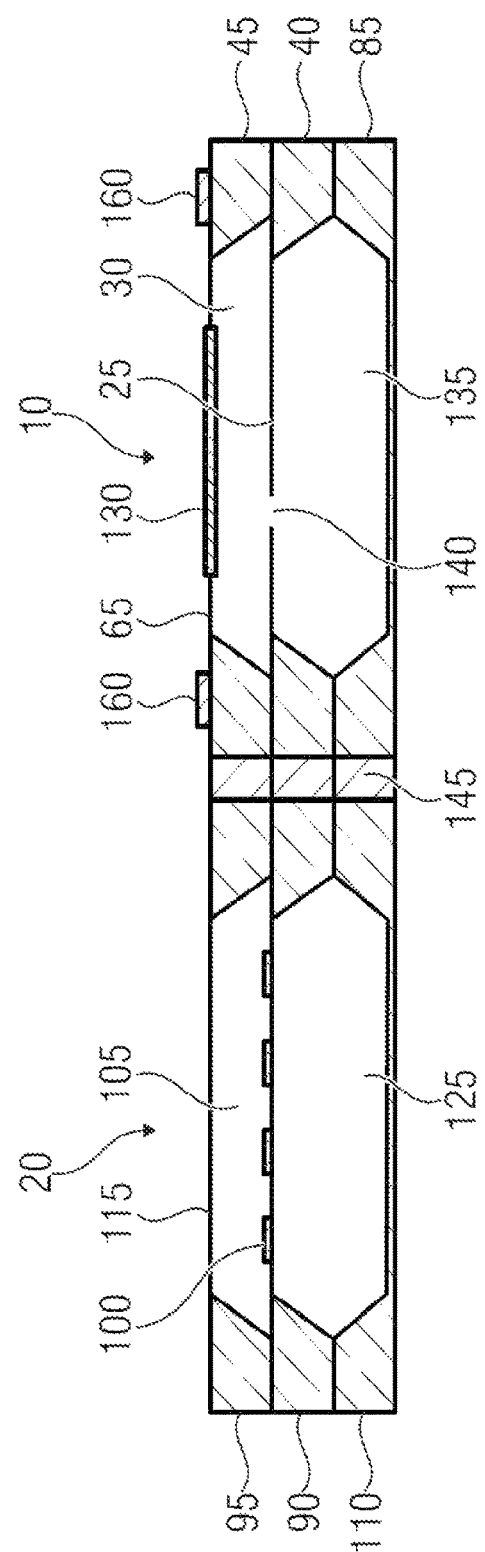
FIG. 2c shows a schematic illustration of an emitter element and a sensor element which are used in a gas sensor, in accordance with a further exemplary embodiment.

FIG. 2c shows the exemplary embodiment described in FIG. 2b, wherein FIG. 2b has been complemented by the spacers 160. If the sensor element 10 and the emitter element 20 are assembled as shown in FIG. 4, the measurement chamber can be embodied between the spacers. The emitter element and the MEMS membrane are sealed in the shown exemplary embodiment and do not come into contact with the measurement gas. In addition to the arrangement of the spacer on the sensor element, shown here, the spacer can also be arranged on the emitter element. Furthermore, FIG. 2c shows a sealed layer 115, i.e. the layer 115 does not have an opening 120. Therefore, the measurement gas does not come into contact with the emitter 110. Moreover, a protective gas can be introduced into the cavities 105 and/or 125 in order to reduce a degradation of the emitter.

Figure 2D:
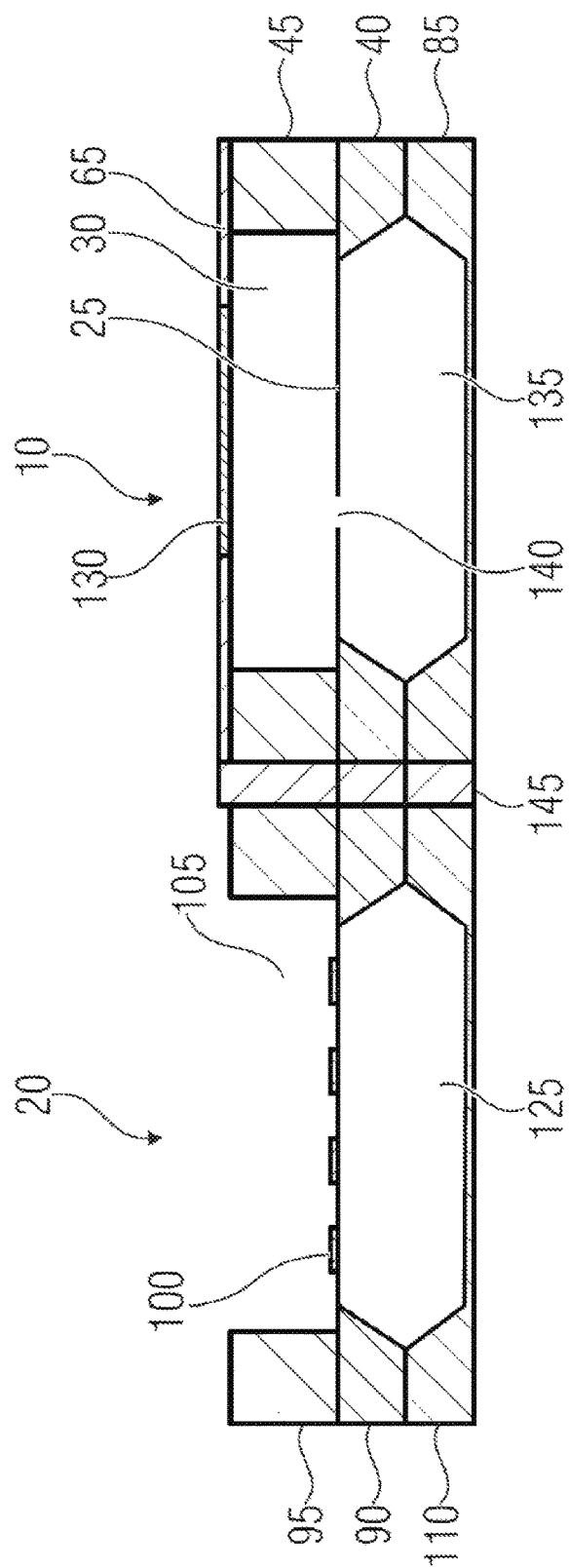
FIG. 2d shows a schematic illustration of an emitter element and a sensor element in an alternative exemplary embodiment with a reference chamber.

FIG. 2d shows a schematic illustration of the sensor element 10 and of the emitter element 20 in accordance with an exemplary embodiment deviating from the one in FIG. 2b. The exemplary embodiment shows the second substrate regions 45, 95 of the sensor element and emitter element, which contain e.g. glass or silicon dioxide ($SiO_2$). This can be a structured glass wafer. It can likewise be connected to the substrate regions lying therebelow by means of anodic bonding at the first substrate region 40 or 90. Furthermore, the cavity 105 in this exemplary embodiment is at least part of the measurement chamber 15, into which a measurement gas to be measured can be introduced. The measurement chamber 15 therefore lies at least in part in the emitter element 20.

Figure 2E:
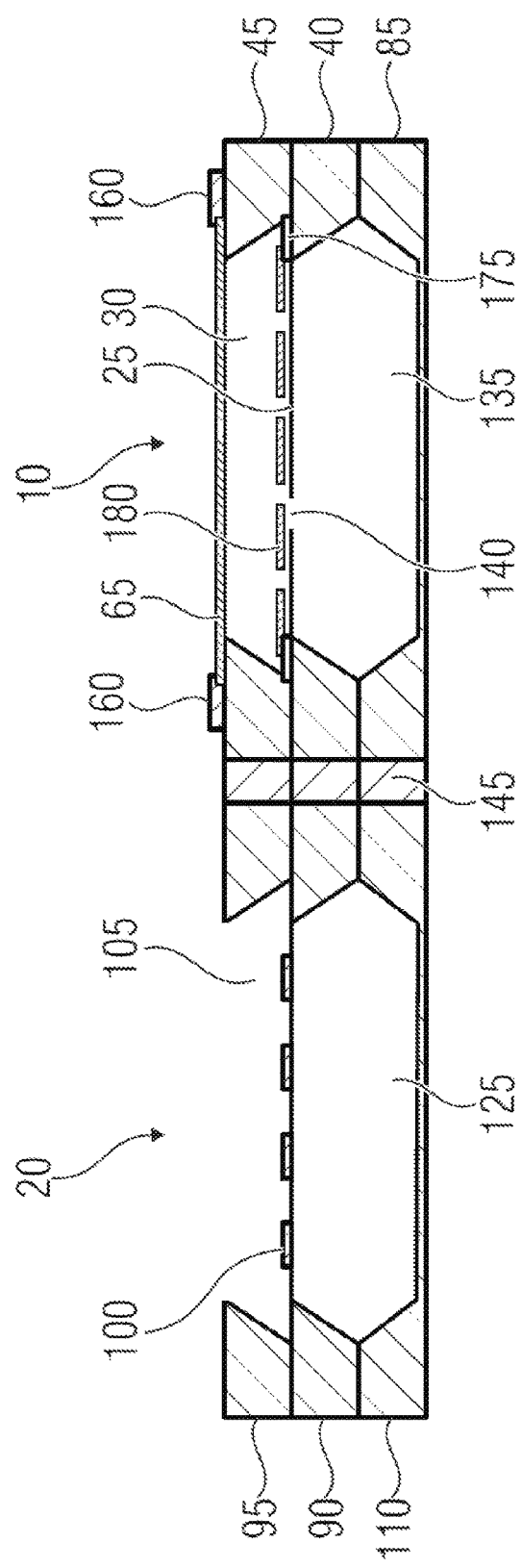
FIG. 2e shows a schematic illustration of an emitter element with a perforated counter electrode lying at the top.

FIG. 2e shows, in a cross section, a schematic illustration of the sensor element 10 and of the emitter element 20. The exemplary embodiment shows an unsealed emitter element 20 and a sealed sensor element 10. An infrared window 65 can be arranged over the second substrate region 45 of the sensor element in order to seal the sensor element 10 in a gastight manner. As already described above, it can be connected to the first substrate region 40 by way of anodic bonding or any other suitable method. Furthermore, the sensor element has a perforated counter electrode 180 lying on the top. The latter can comprise polysilicon, a metal, layers made of a dielectric e.g. SiN (silicon nitride) and a metal or a combination of the aforementioned materials. Preferably, use can be made here of a material which reflects infrared radiation (e.g. a metal). This can be realized by a metalized, perforated counter electrode. The counter electrode 180 forms a functional counterpart to the MEMS membrane in order to form a micromechanical capacitive sensor, for example a microphone. Furthermore, the counter electrode 180 has a perforated embodiment in the shown exemplary embodiment and therefore simultaneously fulfills the task of a shadow mask. The lower the degree of perforation is embodied, the better the shadowing of the MEMS membrane 25 is. The counter electrode can be fastened to a holding structure 175, which e.g. contains an oxide.

Furthermore, it is also possible only to seal the emitter element or emitter in a gastight manner. The sensor element remains open. A heating of the measurement gas can thus be avoided, for example, by a confinement of the emitter unit, for example of the heating wire, such that only the emitted infrared radiation is incident on the measurement gas and it causes the photoacoustic signal there, which signal can be measured by the sensor element. An expansion of the measurement gas as a result of the heating, which is transferred to the MEMS membrane and is superimposed on the photoacoustic signal, is therefore avoided.

FIG. 3 shows, in a schematic illustration, the arrangement, already shown in FIG. 2d, of emitter element and sensor element in a housing 150. The housing 150 has entrance and exit openings 155a, b for the measurement gas 50, through which the measurement gas 50 can enter into the housing 150. By way of example, the housing 150 is an SMD (surface mounted device) housing. Furthermore, the housing 150 has main surface regions on a side facing the sensor element and the emitter element, which main surface regions are embodied to reflect the electromagnetic radiation 55 from the emitter element 20 onto the sensor element 10.

FIG. 4a shows a schematic illustration of a gas sensor in accordance with one exemplary embodiment, wherein the emitter element and the sensor element are stacked in the thickness direction. The gas sensor is based on the arrangement of the emitter element and the sensor element already shown in FIG. 2a. In order to obtain the exemplary embodiment shown in FIG. 4a, the sensor element can be separated from the emitter element along the saw mark 145 shown in FIG. 2a and be stacked on outer main surface regions of the respective second substrate regions. A spacer 160 can preferably be arranged between the sensor element and the emitter element, which spacer forms the measurement chamber 15 between the sensor element and the emitter element. The spacer 160 can be e.g. a connecting element, which was generated by connecting the adjoining substrate regions. Furthermore, the spacers can comprise a semiconductor material (e.g. silicon) or glass. Measurement gas can be introduced into the measurement chamber through an opening in the spacer 160. Taking into account the absence of a reference chamber, the further exemplary embodiments described with reference to the following figures can also be applied to the exemplary embodiment shown here in an analogous manner.

FIG. 4b shows a schematic illustration of a gas sensor in accordance with one exemplary embodiment, wherein the emitter element and the sensor element are stacked in the thickness direction. The gas sensor is based on the arrangement of the emitter element and the sensor element already shown in FIG. 2b. In order to obtain the exemplary embodiment shown in FIG. 4b, the sensor element can be separated from the emitter element along the saw mark 145 shown in FIG. 2b and stacked on outer main surface regions of the respective second substrate regions. A spacer 160 can preferably be arranged between the sensor element and the emitter element, which spacer forms the measurement chamber 15 between the sensor element and the emitter element. The spacer 160 can be e.g. a connecting element, which was generated by connecting the adjoining substrate regions. Furthermore, the spacers can comprise a semiconductor material (e.g. silicon) or glass. Measurement gas can be introduced into the measurement chamber through an opening in the spacer 160.

As already described, the sensor element and the emitter element can be connected together with the spacer, for example by means of anodic bonding or a different bonding method. Furthermore, the spacer itself can also be embodied by a suitable connection material, for example of a connection layer in the case of a bonding method with an intermediate layer, as is used, for example, in eutectic bonding, glass frit bonding or adhesive bonding. This arrangement is advantageous since the measurement gas 50 (not shown here) does not come into contact with either the emitter element or the sensor element in the measurement chamber 15, but rather it is present in a defined region between the sensor element and the emitter element, which is delimited by the spacer 160 and the layers 65 and 115 transmissive to the electromagnetic radiation. This avoids a potential contamination and an accelerated degradation, caused by the measurement gas, of the sensor element and the emitter element. In other words, the sensor element and the emitter element themselves are closed off or sealed.

Exemplary embodiments show the gas sensor in a manner sensitive to carbon dioxide ($CO_2$). By way of example, a carbon dioxide concentration in the measurement gas can have 1000 ppm (parts per million). A reference fluid, which e.g. comprises 50 to 100% carbon dioxide and, optionally, a buffer gas component, can be present in the reference chamber and the pressure equalization chamber 30, 135. Optionally, the buffer gas filling can also furthermore be present in the hollow space 125. If the buffer gas is present adjacent to the emitter unit, i.e. in the cavities 105 or 125, it can serve as an inert protective gas, i.e. slow down a degradation of the emitter. Nitrogen, argon or other heavy gases, which prevent or at least slow down a surface modification, e.g. caused by a great heat of the emitter, can serve as a protective gas.

Alternatively, or in a complementary manner, the buffer gas at the emitter can also serve to filter the output radiation in order to (further) restrict comparatively broadband electromagnetic radiation from the emitter unit in its bandwidth such that more narrowband electromagnetic radiation is incident on the measurement gas. The comparatively broadband electromagnetic radiation at the emitter can have a bandwidth of between 1 µm and 10 µm, with the filtered more narrowband electromagnetic radiation for example having a bandwidth of between 0.2 µm and 0.5 µm. In order to obtain the measurement accuracy of the gas sensor, it is advantageous that the buffer gas is free from the measurement gas to be determined. A filter function can also be achieved by a suitable separation of the emitter from the measurement chamber. By way of example, the layer 115 transmissive to the electromagnetic radiation is therefore embodied as a filter element. This can be achieved by a special treatment of a glass pane or the use of a Fabry-Perot filter.

If the buffer gas is present adjacent to the MEMS membrane 25 or in the reference chamber, it can likewise fulfill the function of a protective gas for the MEMS membrane. Alternatively, or in a complementary manner, it can also comprise as a reference the measurement gas to be determined, i.e., for example, the gas to be measured or the gas mixture to be measured.

The exemplary embodiment shows the emitter element 20 and the sensor element 10 arranged in a projection plane extending in the thickness direction to the emitter element and the sensor element, wherein the second substrate region of the sensor element is connected to the emitter element in a hermetically sealed manner. As already described, the spacer 160 can be inserted between the emitter element and the sensor element. The connection is advantageously brought about by means of anodic bonding or another suitable method for connecting substrate regions. For the purposes of electrical contacting of the emitter element and the sensor element, connectors of the sensor unit and the MEMS membrane, which e.g. can be contacted by way of contact pads, can be embodied between the second and the third substrate regions or between the first and the second substrate regions of the sensor element and the emitter element.

Figure 4C:
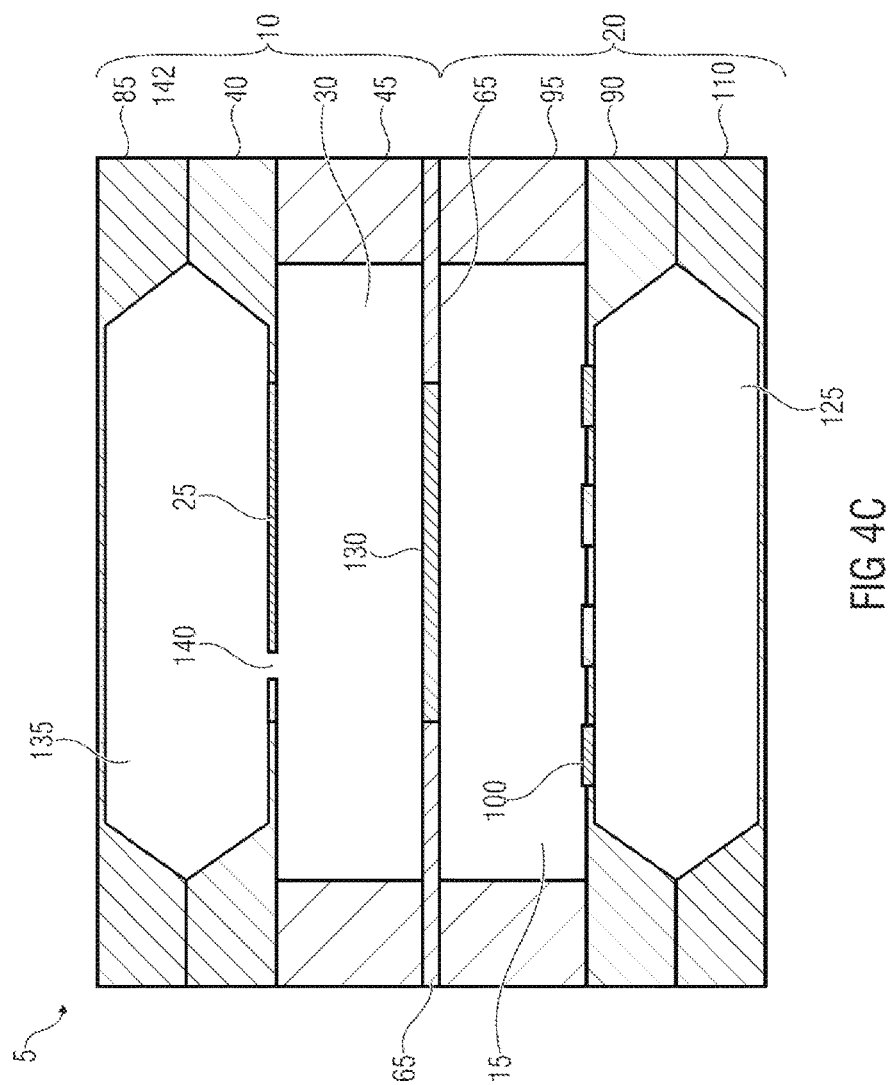
FIG. 4c shows a schematic illustration of a gas sensor with a reference chamber in an exemplary embodiment deviating from the one in FIG. 4b.

FIG. 4c shows a schematic illustration of the gas sensor 5, which is constructed on the basis of the sensor element 10 and the emitter element 20 of the exemplary embodiment shown in FIG. 2d. As already described with respect to FIG. 4b, the sensor element and the emitter element can be separated at the saw mark 145 such that the second substrate region in the sensor element can be connected to the second substrate region of the emitter element in such a way that a gas sensor that is stacked in the thickness direction is created, which gas sensor comprises six substrate regions in the shown exemplary embodiment. The shown exemplary embodiment has a sealed microphone 25, whereas the measurement chamber is integrated into the emitter element and is in direct contact with the emitter unit 100. This exemplary embodiment allows the smallest embodiment of the gas sensor 5 in the x-, y- and z-direction.

Figure 5A:
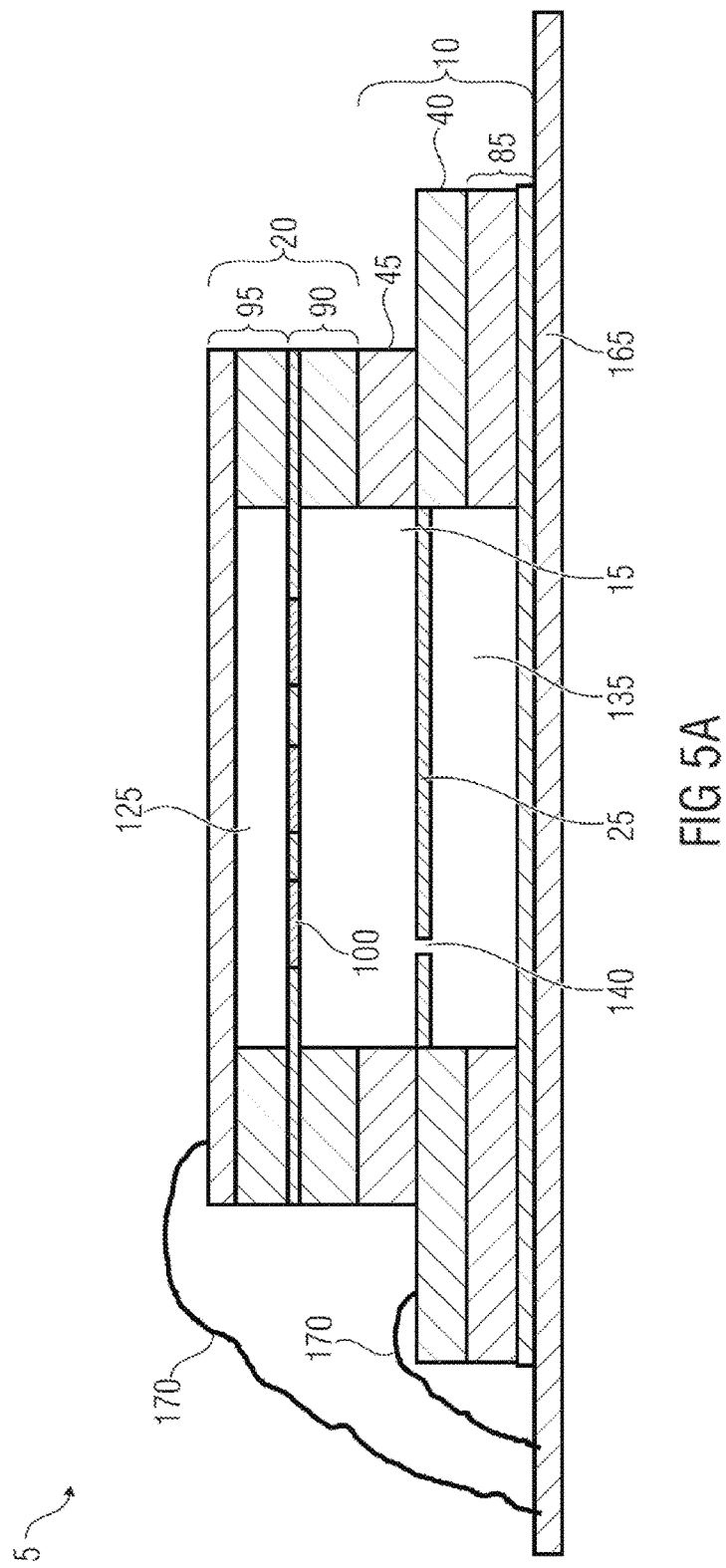
FIG. 5a shows a schematic illustration of a gas sensor in accordance with one exemplary embodiment, with exemplary contacting of the gas sensor.

FIG. 5a shows a schematic illustration of the gas sensor 5 in accordance with an exemplary embodiment without a reference chamber, which is based on the exemplary embodiments shown in FIG. 2a and FIG. 4a. The embodiment of the emitter element 20, in which the first substrate region 90 is rotated by 180° about an axis extending laterally through the substrate region, deviates from the aforementioned exemplary embodiments. The emitter unit 100 can be arranged superficially on the substrate region 90 and be exposed on the rear side, for example by etching, from an opposite main surface region. Hence, the emitter element 20 can be operated on the rear side. The same principle is also applicable to the MEMS membrane 25 in the first substrate region 40 of the sensor element, but this is not explicitly shown in the figures.

Furthermore, FIG. 5a shows contacting of the gas sensor 5 on a printed circuit board (PCB) 165, which is explained in more detail on the basis of the following figures. Contacting in accordance with the TSV 170' described in FIG. 5b is likewise possible, just as the other exemplary embodiments, which are described with respect to FIGS. 5b-d, are applicable to FIG. 5a.

Figure 5B:
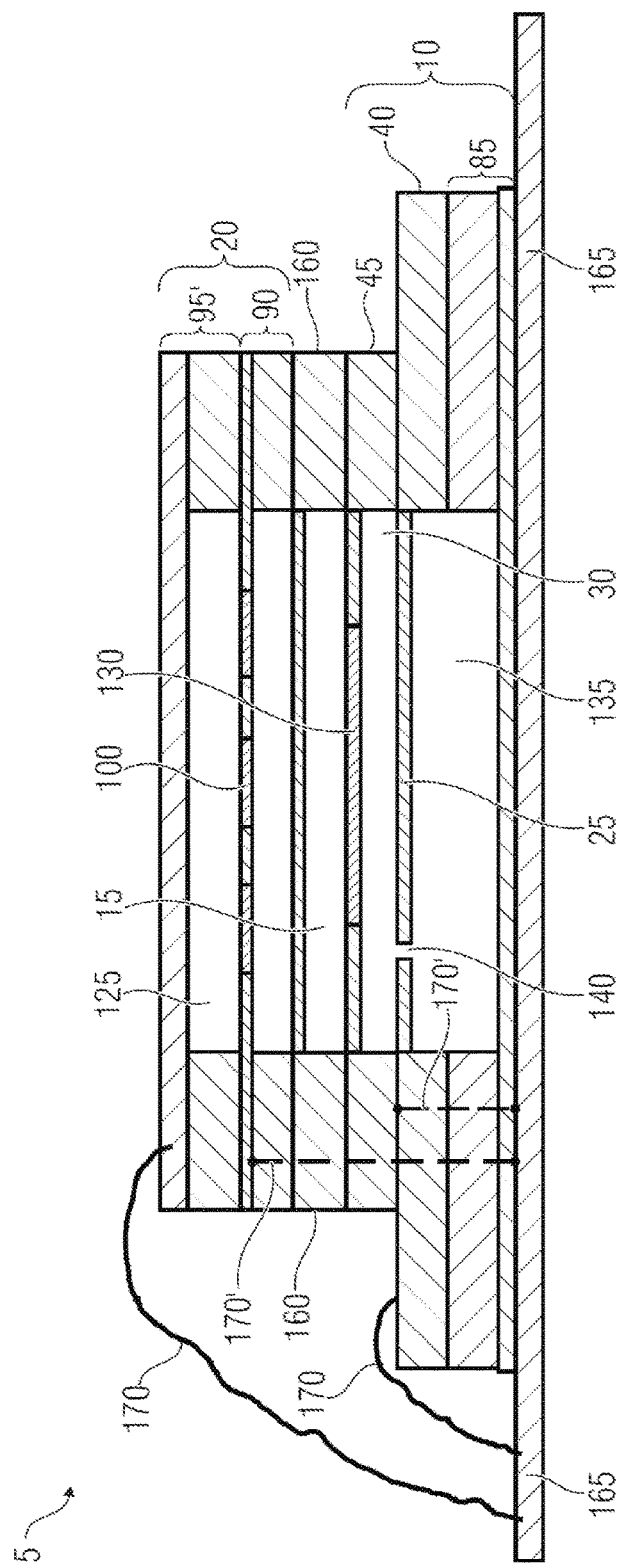
FIG. 5b shows a schematic illustration of a gas sensor in accordance with one exemplary embodiment with a reference chamber and with exemplary contacting of the gas sensor.
Figure 5D:
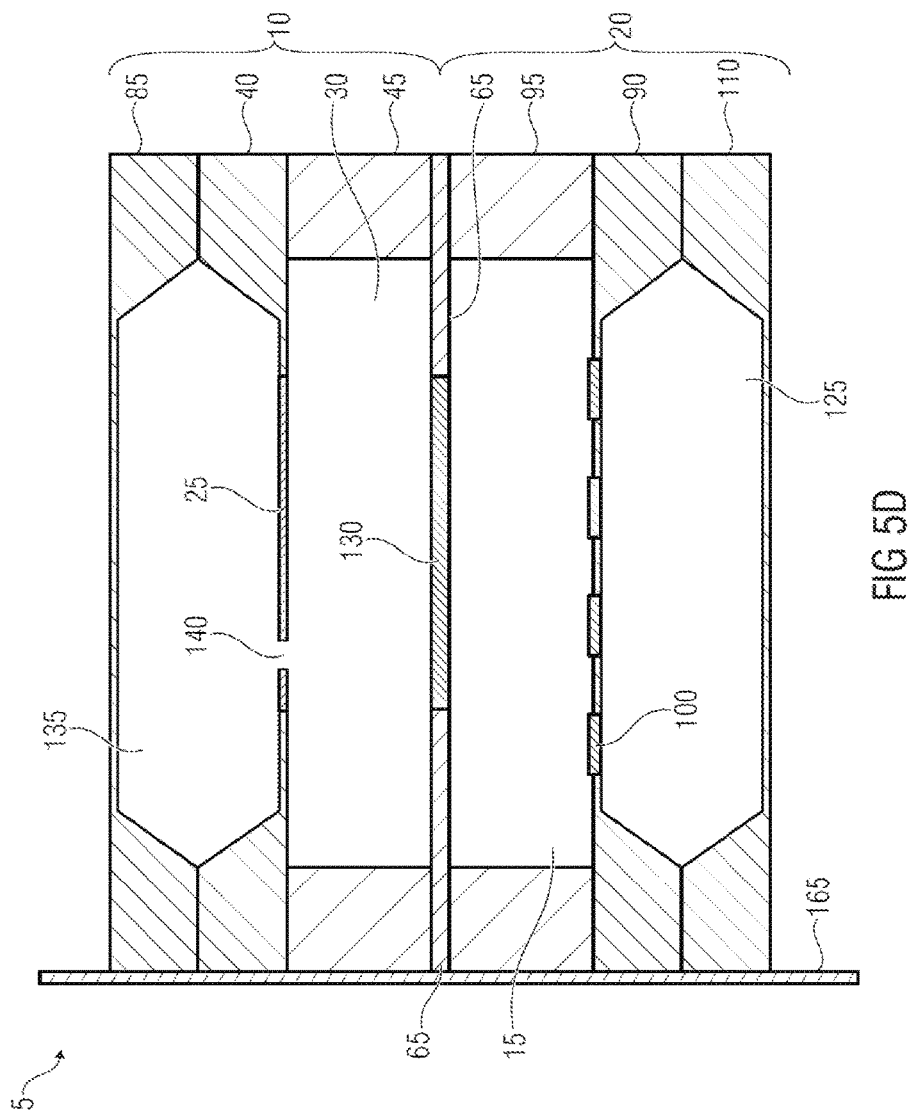
FIG. 5d shows a schematic illustration of a gas sensor in accordance with one exemplary embodiment with deviating contacting of the gas sensor.

FIG. 5b shows a schematic illustration of the gas sensor 5 in accordance with an exemplary embodiment, which is based on the exemplary embodiments shown in FIG. 2b and FIG. 4b. The embodiment of the emitter element 20, in which the first substrate region 90 is rotated by 180° about an axis extending laterally through the substrate region, deviates from the aforementioned exemplary embodiments. The emitter unit 100 can be arranged superficially on the substrate region 90 and be exposed on the rear side, for example by etching, from an opposite main surface region. Hence, the emitter element 20 can be operated on the rear side. The same principle is also applicable to the MEMS membrane 25 in the first substrate region 40 of the sensor element, but this is not explicitly shown in the figures.

Furthermore, FIG. 5b shows contacting of the gas sensor 5 on a printed circuit board (PCB) 165. FIG. 5b shows the contacting by means of contact elements 170, for example by means of wires, which contact contacts of the gas sensor 5, embodied toward the outside, with the conductor track 165. To this end, it is advantageous if the substrate plane 40 of the sensor element has a greater diameter than the substrate regions lying thereabove, as shown in FIG. 5b. Hence, contact structures of the MEMS membrane 25 can be exposed at a main surface region of the first substrate region 40. The contacts of the emitter unit 100 are likewise embodied at a main surface region and connected to the conductor track 165 by way of a contact element 170.

Alternatively, the connectors of the MEMS membrane 25 and of the emitter unit 100 can be guided in the interior of the substrate regions to the conductor track 165, for example by means of TSV 170', and be contacted to said conductor track there.

It is likewise possible, but not shown, to guide e.g. the connector of the emitter unit 100 to a substrate plane of the MEMS membrane and undertake the contacting with both contacting elements 170 there.

FIG. 5c shows an exemplary embodiment, which is based on the exemplary embodiments of FIGS. 2d and 4c. As already described in FIG. 5b, the emitter unit 100 is operated on the rear side. Furthermore, the etched cavity of the substrate region 90 is embodied as a measurement chamber 15. As already described with respect to FIG. 5b, FIG. 5c shows the contacting of the printed circuit board 165 by means of the contacting elements 170.

FIG. 5d shows a further contacting option on the basis of the exemplary embodiment from FIG. 4c. In accordance with this exemplary embodiment, contacts of the emitter element and the sensor element are embodied laterally on a main surface region of the emitter element and the sensor unit. The laterally embodied contacts are directly contacted with the printed circuit board 165, which is arranged parallel to a thickness direction of the emitter element and the sensor element.

Although some aspects have been described in connection with a device, it goes without saying that these aspects also represent a description of the corresponding method, such that a block or a component of a device should also be understood as a corresponding method step or as a feature of a method step. Analogously to this, aspects described in connection with or as a method step also represent a description of a corresponding block or detail or feature of a corresponding device.

The exemplary embodiments described above merely constitute an illustration of the principles of the present disclosure. It goes without saying that modifications and variations of the arrangements and details described herein will become apparent to other persons skilled in the art. Therefore, the intention is for the disclosure to be restricted only by the scope of protection of the following patent claims, and not by the specific details presented herein on the basis of the description and the explanation of the exemplary embodiments.

The invention claimed is:
1. A gas sensor, comprising:
a sensor element comprising;
a first substrate, comprising a MEMS membrane associated with the sensor element; and
a second substrate arranged on top of the first substrate, wherein the first substrate and the second substrate define at least a portion of a reference gas chamber;
an emitter element comprising:

an emitter unit arranged beside the MEMS membrane on the first substrate and configured to emit electromagnetic radiation; and an emitter cavity arranged above the emitter unit;

a measurement chamber above the second substrate, which is embodied to receive a measurement gas, wherein the measurement chamber includes at least one surface region configured to reflect electromagnetic radiation from the emitter unit onto the sensor element; and wherein the emitter element and the sensor element are arranged in a stationary manner with respect to one another.

2. The gas sensor as claimed in claim 1, wherein the MEMS membrane is embodied to have a deflection which is dependent on the energy of the electromagnetic radiation present.

3. The gas sensor as claimed in claim 1, wherein the emitter unit is embodied to emit the electromagnetic radiation in a pulsating manner with a frequency that is greater than 0.1 Hz or greater than 0.5 Hz or greater than 1 Hz.

4. The gas sensor as claimed in claim 1, further comprising a third substrate arranged under the first substrate, wherein the third substrate at least partially defines a pressure equalization chamber.

5. The gas sensor as claimed in claim 4, wherein the third substrate defines at least a portion of a second emitter cavity disposed adjacent to the emitter element.

6. The gas sensor as claimed in claim 1, wherein the second substrate further comprises a shadow mask arranged above the MEMS membrane.

7. The gas sensor as claimed in claim 1, wherein contacts of the emitter element and of the sensor element are guided by means of a through semiconductor via (TSV) within the emitter element and the sensor element to a common substrate plane and embodied at a main surface region of the gas sensor that is accessible from outside.

8. The gas sensor as claimed in claim 1, wherein contacts of the emitter element and the sensor element are embodied laterally at a surface region of the emitter element and the sensor element, wherein a printed circuit board is arranged parallel to a thickness direction of the emitter element and the sensor element and contacts the laterally embodied contacts.

9. The gas sensor as claimed in claim 1, wherein the MEMS membrane forms a micromechanical capacitive sensor.

10. The gas sensor as claimed in claim 1, wherein the MEMS membrane is embodied as a microphone.

11. The gas sensor as claimed in claim 1, wherein the emitter element is embodied as a microelectromechanical emitter.

* * * * *